(12) United States Patent
Mathews

(10) Patent No.: US 8,412,470 B2
(45) Date of Patent: Apr. 2, 2013

(54) CHANGE MAPPING FOR STRUCTURAL HEALTH MONITORING

(75) Inventor: V. John Mathews, Salt Lake City, UT (US)

(73) Assignee: The Boeing Company, Chicago, IL (US)

( * ) Notice: Subject to any disclaimer, the term of this patent is extended or adjusted under 35 U.S.C. 154(b) by 1238 days.

(21) Appl. No.: 12/189,288

(22) Filed: Aug. 11, 2008

(65) Prior Publication Data

US 2010/0036617 A1 Feb. 11, 2010

(51) Int. Cl.
*G01B 3/44* (2006.01)

(52) U.S. Cl. .......................................... 702/34

(58) Field of Classification Search .............. 702/34, 702/35, 36, 39, 185
See application file for complete search history.

(56) References Cited

U.S. PATENT DOCUMENTS

| | | | |
|---|---|---|---|
| 6,006,163 A | 12/1999 | Lichtenwalner et al. | |
| 6,484,132 B1 | 11/2002 | Hively et al. | |
| 6,958,686 B2 | 10/2005 | Okubo | |
| 7,000,478 B1 | 2/2006 | Zwollo et al. | |
| 7,061,229 B2 | 6/2006 | Townsend et al. | |
| 7,286,964 B2 * | 10/2007 | Kim .............. | 702/183 |
| 7,324,193 B2 | 1/2008 | Lally et al. | |
| 7,374,539 B2 | 5/2008 | Fernando et al. | |
| 7,487,059 B2 | 2/2009 | Davis et al. | |
| 7,498,576 B2 | 3/2009 | Micko | |
| 7,552,027 B2 | 6/2009 | Kearns et al. | |
| 7,720,626 B2 | 5/2010 | Mathews | |
| 7,726,875 B2 | 6/2010 | Yuhas | |
| 7,822,573 B2 | 10/2010 | Ihn | |
| 7,842,874 B2 | 11/2010 | Jehan | |
| 7,937,248 B2 | 5/2011 | Ihn et al. | |
| 7,991,587 B2 | 8/2011 | Ihn | |
| 8,055,455 B2 | 11/2011 | Ihn et al. | |
| 8,127,610 B2 | 3/2012 | Mathews | |
| 2007/0291958 A1 | 12/2007 | Jehan | |
| 2008/0319692 A1 | 12/2008 | Davis et al. | |
| 2009/0083004 A1 | 3/2009 | Ihn et al. | |
| 2010/0036618 A1 | 2/2010 | Mathews et al. | |

OTHER PUBLICATIONS

GB Search Report dated Nov. 5, 2008 regarding application No. GB0812572.6, applicant's reference P10502GB00, 3 pages.
USPTO Office Action dated Sep. 8, 2009 for U.S. Appl. No. 12/235,142, 10 pages.
USPTO Notice of Allowance dated Jan. 4, 2010 for U.S. Appl. No. 12/235,142, 7 pages.
USPTO Office Action dated Nov. 29, 2010 for U.S. Appl. No. 12/189,293, 12 pages.
USPTO Office Action dated Jun. 13, 2011 for U.S. Appl. No. 12/189,293, 11 pages.
USPTO Notice of Allowance dated Nov. 2, 2011 for U.S. Appl. No. 12/189,293, 8 pages.
USPTO Notice of Allowance dated Apr. 11, 2011 for U.S. Appl. No. 12/189,293, 2 pages.
USPTO Office Action dated Sep. 23, 2010 for U.S. Appl. No. 12/851,408, 15 pages.
USPTO Notice of Allowance dated Mar. 21, 2011 for U.S. Appl. No. 12/851,408, 7 pages.

(Continued)

*Primary Examiner* — Stephen Cherry
(74) *Attorney, Agent, or Firm* — Yee & Associates, P.C.

(57) ABSTRACT

A method is present for mapping changes in a structure. A plurality of responses is collected from a set of transmitter and sensor pairs for the structure. Change metrics for pixels in a plurality of grids are identified from the plurality of responses, wherein a first grid in the plurality of grids is shifted in relation to a second grid in the plurality of grids. A map is generated for the structure using the change metrics.

16 Claims, 11 Drawing Sheets

OTHER PUBLICATIONS

USPTO Final Office Action dated Jan. 13, 2012 for U.S. Appl. No. 12/189,423, 10 pages.
USPTO Final Office Action dated Feb. 14, 2011 for U.S. Appl. No. 12/189,423, 8 pages.
USPTO Office Action dated Oct. 15, 2010 for U.S. Appl. No. 12/189,423, 9 pages.
USPTO Office Action dated Sep. 23, 2011 for U.S. Appl. No. 12/189,423, 8 pages.
USPTO Office Action dated Nov. 4, 2009 for U.S. Appl. No. 12/840,427, 12 pages.
USPTO Office Action dated Apr. 22, 2010 for U.S. Appl. No. 12/840,427, 12 pages.
USPTO Notice of Allowance dated Feb. 19, 2010 for U.S. Appl. No. 12/840,427, 8 pages.
USPTO Notice of Allowance dated Jun. 16, 2010 for U.S. Appl. No. 12/840,427, 9 pages.
USPTO Final Office Action dated Nov. 17, 2010 for U.S. Appl. No. 12/135,591, 10 pages.
USPTO Office Action dated Aug. 3, 2010 for U.S. Appl. No. 12/135,591, 12 pages.
USPTO Notice of Allowance dated Jul. 6, 2011 for U.S. Appl. No. 12/135,591, 8 pages.
Croxford et al., "Strategies for overcoming the effects of temperature on guided wave structural health monitoring", Proceedings of the SPIE Conference on Health Monitoring and Smart Nondestructive Evaluation of Structural and Biological Systems III, vol. 6532, SPIE, 2007, pp. 6531T-1-10 (Abstract).
Kovvali et al., "Time-Frequency based Classification of Structural Damage", Proceedings of 48th AIAA/ASME/ASCE/AHS/ASC Structures, Structural Dynamics, and Materials Conference, Apr. 2007, 11 pages.
Leonard et al., "Ultrasonic Lamb wave tomography", Inverse Problems, vol. 18, No. 6, Dec. 2002, pp. 1795-1808.
Leutenegger et al., "Detection of defects in cylindrical structures using a time reverse method and a finite-difference approach", Ultrasonics, vol. 40, Issue 10, May 2002, pp. 721-725.
Leutenegger et al., "Non-destructive testing of tubes using a time reverse numerical simulation (TRNS) method", Ultrasonics, vol. 41, May 2004, pp. 811-822.
Lynch et al., "Design of a Wireless Active Sensing Unit for Structural Health Monitoring", Proceedings of SPIE 11th Annual International Symposium on Smart Structures and Materials, Mar. 2004, 12 pages.
"Vibration Sensor (SDT1-028K)", Measurement Specialties, Oct. 1998, 2 pages.
Park et al., "Vibration Testing and Analysis of Inflatable Structures using Smart Materials", Proceedings of 2001 ASME International Mechanical Engineering Congress and Exposition, Nov. 2001, 8 pages.
"Installation Drawing Model 352C22 Accelerometer", PCB Piezotronics, Apr. 2003, 2 pages.
"Model 352C22 Spec Sheet", PCB Piezotronics, retrieved Nov. 3, 2011, 2 pages http://pcb.com/spec_sheet.asp?model=352C22.
Prasad et al., "Structural health monitoring of composite structures using Lamb wave tomography", Smart Materials and Structures, vol. 13, No. 5, Oct. 2004, pp. N73-N79 (Abstract).
Shi et al., "Identification of Time-Domain Reflectometry Measurement Results by Wavelet Modeling", Proceedings of International Workshop on Structural Health Monitoring, 2001, pp. 1269-1277.
Wang et al., "A synthetic time-reversla imaging method for structural health monitoring", Smart Materials and Structures, vol. 13, No. 2, Apr. 2004, pp. 415-423.
Notice of Allowance, dated Aug. 17, 2012, regarding U.S. Appl. No. 12/189,423, 9 pages.

* cited by examiner

CHANGE MAPPING FOR STRUCTURAL HEALTH MONITORING

BACKGROUND INFORMATION

1. Field

The present disclosure relates generally to processing data and in particular to processing data from responses of a structure to an input wave form. Still more particularly, the present disclosure relates to a method, apparatus, and computer usable program code for identifying anomalies in a structure.

2. Background

Composite and metallic aircraft structures may be susceptible to internal changes that may occur from fatigue, impacts, and other events or conditions. Composite materials typically have a minimal visual indication of these types of changes. As a result, an aircraft may be inspected to access the integrity of the structure on a periodic basis, or after visual indications of surface anomalies, such as dent and scratch.

For example, impacts to a structure, such as an aircraft, may occur during cargo loading and unloading. Inspections of the structure of an aircraft may be time consuming and costly in terms of the time and skill needed to perform the inspection. Further, an airline may incur lost revenues from the aircraft being out of service.

Health monitoring techniques have been developed and used to monitor structures. These techniques often build the health monitoring systems into the structures. These health monitoring systems may be used to determine whether changes have occurred to these materials and structures over time.

Sudden changes in environments, such as electromagnetic effects, mechanical stresses, and other environmental effects may affect the integrity of various materials and structures over time. By having health monitoring systems built into or associated with the structures to monitor the structures during use, appropriate measures and responses may be taken to prevent catastrophic failures and may prolong the life span of these structures.

The monitoring of structures may include various nondestructive elevation methods, such as ultrasonic testing or x-ray testing. Ultrasonic testing uses contact-based transducers to mechanically scan a structure. These distributed sensors and actuators may be surface mounted on the structure or may be embedded in the structure to generate and propagate control of diagnostic signals into the structure being monitored.

A structural health monitoring system is based on using a transmitter and a sensor configuration to transmit waveforms at various frequency ranges and acquire data from the responses. Often times, transducers may function both as a transmitter and a sensor. Although structural health monitoring systems may provide an automated on board system for detecting characterizing anomalies or changes that may require maintenance, inspection, or other actions.

SUMMARY

In one advantageous embodiment, a method is present for mapping changes in a structure. A plurality of responses is collected from a set of transmitter and sensor pairs for the structure. Change metrics for pixels in a plurality of grids are identified from the plurality of responses, wherein a first grid in the plurality of grids is shifted in relation to a second grid in the plurality of grids. A map is generated for the structure using the change metrics.

In another advantageous embodiment, an apparatus comprises a structure having a set of components, a set of transmitters physically associated with the set of components, a set of sensors physically associated with the set of components, and a data processing system. The set of sensors is capable of detecting response to the signals. The set of transmitters is capable of sending signals into the set of components. The structural health monitoring system is in communication with the set of transmitters and the set of sensors. The structural health monitoring system is capable of collecting a plurality of responses from the set of transmitters and the set of sensors; identifying change metrics for pixels in a plurality of grids from the plurality of responses, wherein a first grid in the plurality of grids is shifted in relation to a second grid in the plurality of grids; and generating a map for the structure using the change metrics.

In yet another advantageous embodiment, a computer program product comprises a computer recordable storage medium and program code. Program code is present for collecting a plurality of responses from a set of transmitter and sensor pairs for a structure. Program code is also present for identifying change metrics for pixels in a plurality of grids from the plurality of responses, wherein a first grid in the plurality of grids is shifted in relation to a second grid in the plurality of grids. Program code is present for generating a map for the structure using the change metrics.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
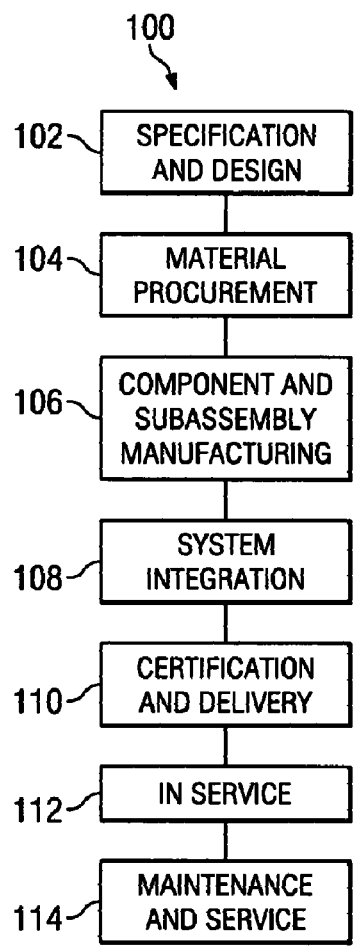
FIG. 1 is a diagram illustrating an aircraft manufacturing and service method in which an advantageous embodiment may be implemented.
Figure 2:
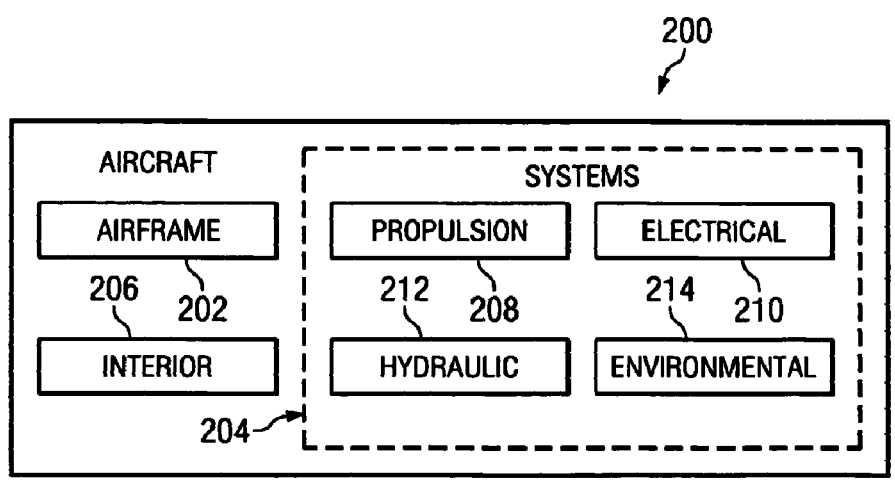
FIG. 2 is a diagram of an aircraft in accordance with an advantageous embodiment.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

In one illustrative example, health monitoring systems of the advantageous embodiments may be implemented during component sub-assembly manufacturing 106 in system integration 108. In other advantageous embodiments, health monitoring systems may be added or implemented during maintenance and service 114. In these advantageous embodiments, health monitoring systems may include a method and apparatus for mapping changes that may be identified during the monitoring of structures.

Figure 3:
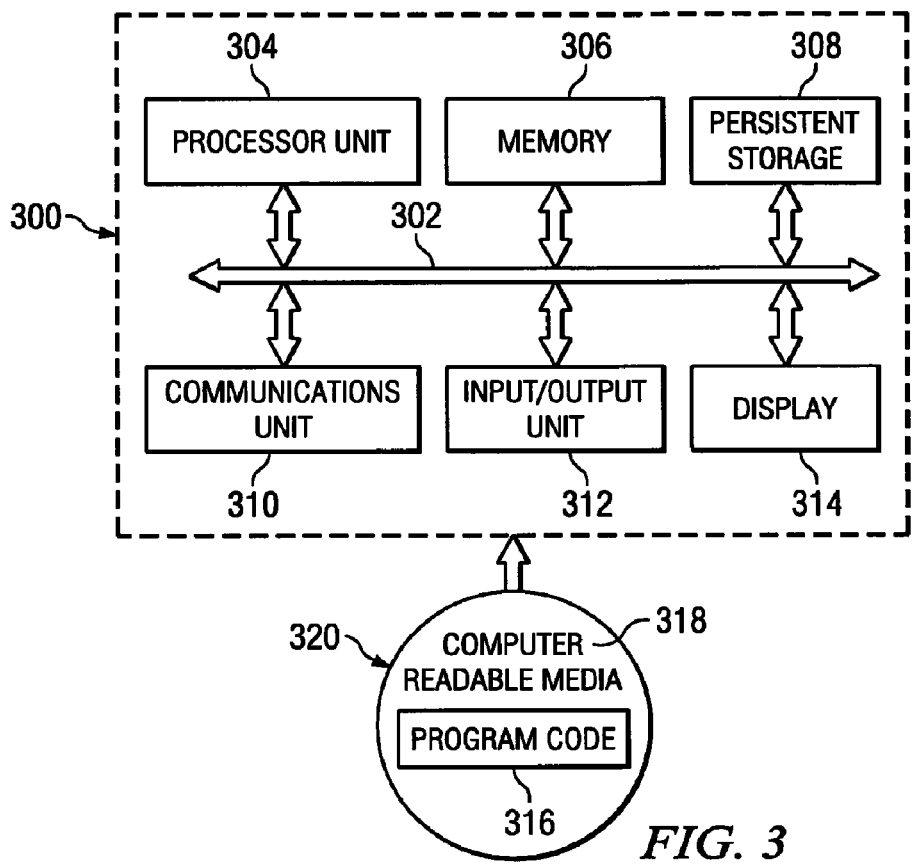
FIG. 3 is a diagram of a data processing system in accordance with an advantageous embodiment.

Turning now to FIG. 3, a diagram of a data processing system is depicted in accordance with an advantageous embodiment. In these examples, data processing 300 may implement processes to estimate change metrics in accordance with advantageous embodiments. These change metrics may be used to determine whether an anomaly or change is present in a structure. These change metrics may be used to identify the similarity indexes for the structure.

A dissimilarity index is a value used to determine whether a structure is changed as compared to a previous time when the structure was interrogated or monitored. A change metric is used to describe a value of a particular portion of a map, such as a pixel. In this illustrative example, data processing system 300 includes communications fabric 302, which provides communications between processor unit 304, memory 306, persistent storage 308, communications unit 310, input/output (I/O) unit 312, and display 314.

Processor unit 304 serves to execute instructions for software that may be loaded into memory 306. Processor unit 304 may be a set of one or more processors or may be a multi-processor core, depending on the particular implementation. Further, processor unit 304 may be implemented using one or more heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices. A storage device is any piece of hardware that is capable of storing information either on a temporary basis and/or a permanent basis. Memory 306, in these examples, may be, for example, a random access memory or any other suitable volatile or non-volatile storage device.

Persistent storage 308 may take various forms depending on the particular implementation. For example, persistent storage 308 may contain one or more components or devices. For example, persistent storage 308 may be a hard drive, a flash memory, a rewritable optical disk, a rewritable magnetic tape, or some combination of the above. The media used by persistent storage 308 also may be removable. For example, a removable hard drive may be used for persistent storage 308.

Communications unit 310, in these examples, provides for communications with other data processing systems or devices. In these examples, communications unit 310 is a network interface card. Communications unit 310 may provide communications through the use of either or both physical and wireless communications links.

Input/output unit 312 allows for input and output of data with other devices that may be connected to data processing system 300. For example, input/output unit 312 may provide a connection for user input through a keyboard and mouse. Further, input/output unit 312 may send output to a printer. Display 314 provides a mechanism to display information to a user.

Instructions for the operating system and applications or programs are located on persistent storage 308. These instructions may be loaded into memory 306 for execution by processor unit 304. The processes of the different embodiments may be performed by processor unit 304 using computer implemented instructions, which may be located in a memory, such as memory 306.

These instructions are referred to as program code, computer usable program code, or computer readable program code that may be read and executed by a processor in processor unit 304. The program code in the different embodiments may be embodied on different physical or tangible computer readable media, such as memory 306 or persistent storage 308.

Program code 316 is located in a functional form on computer readable media 318 that is selectively removable and may be loaded onto or transferred to data processing system 300 for execution by processor unit 304. Program code 316 and computer readable media 318 form computer program product 320 in these examples.

In one example, computer readable media 318 may be in a tangible form, such as, for example, an optical or magnetic disc that is inserted or placed into a drive or other device that is part of persistent storage 308 for transfer onto a storage device, such as a hard drive that is part of persistent storage 308.

In a tangible form, computer readable media 318 also may take the form of a persistent storage, such as a hard drive, a thumb drive, or a flash memory that is connected to data processing system 300. The tangible form of computer readable media 318 is also referred to as computer recordable storage media. In some instances, computer readable media 318 may not be removable.

Alternatively, program code 316 may be transferred to data processing system 300 from computer readable media 318 through a communications link to communications unit 310 and/or through a connection to input/output unit 312. The communications link and/or the connection may be physical or wireless in the illustrative examples. The computer readable media also may take the form of non-tangible media, such as communications links or wireless transmissions containing the program code.

The different components illustrated for data processing system 300 are not meant to provide architectural limitations to the manner in which different embodiments may be implemented. The different illustrative embodiments may be implemented in a data processing system including components in addition to or in place of those illustrated for data processing system 300. Other components shown in FIG. 3 can be varied from the illustrative examples shown.

As one example, a storage device in data processing system 300 is any hardware apparatus that may store data. Memory 306, persistent storage 308, and computer readable media 318 are examples of storage devices in a tangible form.

In another example, a bus system may be used to implement communications fabric 302 and may be comprised of one or more buses, such as a system bus, or an input/output bus. Of course, the bus system may be implemented using any suitable type of architecture that provides for a transfer of data between different components or devices attached to the bus system.

Additionally, a communications unit may include one or more devices used to transmit and receive data, such as a modem or a network adapter. Further, a memory may be, for example, memory 306 or a cache such as found in an interface and memory controller hub that may be present in communications fabric 302.

The different advantageous embodiments may acquire signals during inspections and/or monitoring of the structure. The signals may be referred to as test signals or responses. Baseline signals and test signals may be present for different pairs of sensors and transmitters in a set of transducers. The differences between a baseline signal and a test signal may be identified using an identifier, such as a dissimilarity index. A dissimilarity index is a value associated with a path to indicate whether a change is present in a structure within the path.

The different advantageous embodiments may map this information. This map may take the form of a two-dimensional or three-dimensional map or image. This resulting map represents the state of the structure within the area being monitored. The different advantageous embodiments may use this map to identify changes in the structure. Further, this map also may be used to identify the severity or amount of change by estimating the outline of change within the structure from the different changes in the map.

The different advantageous embodiments recognize and consider that tomography from other fields may be applied to structural health monitoring. These types of approaches, however, require a very dense array of sensors placed around the area being monitored. These types of approaches, when used in structural health monitoring, may constrain the monitoring to a relatively small area to accommodate the number of sensors and desired sensor density. In other implementations, the sensor density may become smaller resulting in a decrease in the resolution of a map identifying changes.

Thus, the different advantageous embodiments provide a method, apparatus, and computer program product for mapping changes in a structure. Responses are collected from a set of transmitter and sensor pairs for the structure. Change metrics are identified for pixels in a plurality of grids from the responses. These change metrics may be used to identify changes in the structure between baseline data acquisition and test data acquisition. A first grid in the plurality of grids is shifted in relation to a second grid in the plurality of grids. A map is generated for the structure using the change metrics for the different grids.

In these examples, each grid in the plurality of grids has a lower resolution than the map that is finally generated using all of the change metrics from all of the grids. In the different advantageous embodiments, the different grids have a first resolution and are combined or placed into a final grid having a second resolution. In these examples, the second grid has a higher resolution and is a grid for the map.

Figure 4:
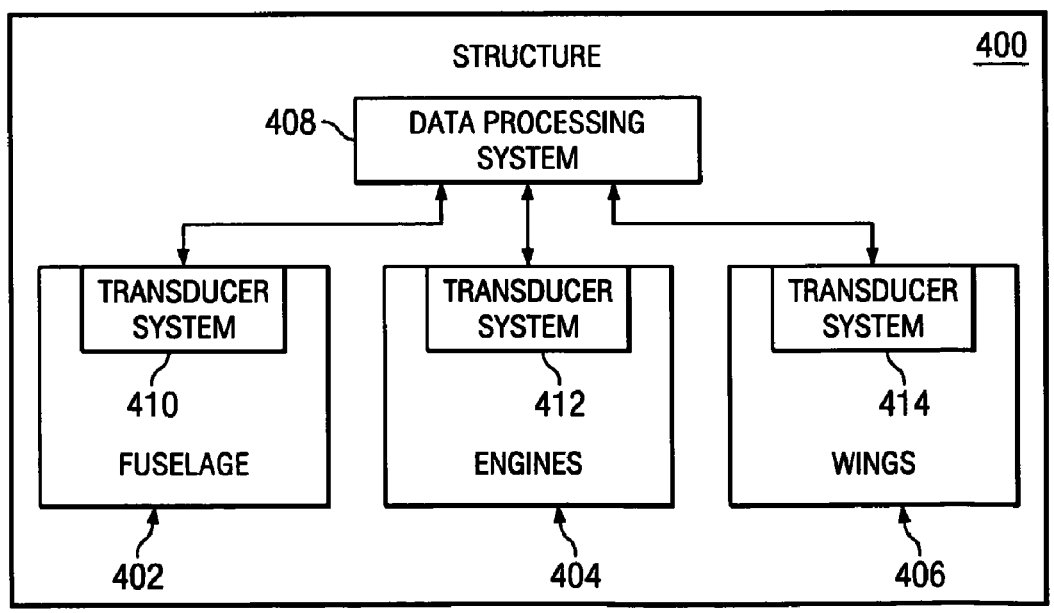
FIG. 4 is a diagram illustrating components used for structural health monitoring in a structure in accordance with an advantageous embodiment.

Turning now to FIG. 4, a diagram illustrating components used for structural health monitoring in a structure is depicted in accordance with an advantageous embodiment. Structure 400 is an example of a structure in which a health monitoring system may be implemented. Structure 400 may take many forms, such as an aircraft, a car, a tank, a ship, a submarine, a spacecraft, a dam, a building, a bridge, or some other suitable structure.

In this example, structure 400 takes the form of an aircraft. Structure 400 includes fuselage 402, engines 404, and wings 406. Other components also may be found in structure 400, but only these depicted ones are presented for purposes of illustrating different features in the different advantageous embodiments.

Structure 400 also includes data processing system 408, transducer system 410, transducer system 412, and transducer system 414. These components form a health monitoring system in these examples. Although transducers are used for transmitters and sensors, in these examples, any type of transmitter, sensor, or device that is capable of sending and detecting signals at the frequencies needed to transmit the signals into a material may be used.

Data processing system 408 may be implemented in structure 400 using a data processing system, such as data processing system 300 in FIG. 3. Data processing system 408 may take the form of software, hardware, or a combination of software and hardware. In this example, data processing system 408 is implemented in software using a data processing system, such as data processing system 300 in FIG. 3.

Transducer systems 410, 412, and 414 are examples of transmitters and sensors that may be implemented in structure 400 to transmit signals and detect responses to those signals. In these examples, the transducers in these systems are "associated" with the particular components in structure 400. A transmitter or sensor, such as those in transducer systems 410, 412, and 414, may be physically associated with the component by being attached to the component or even embedded within the component. In these examples, the transducers are fixed transmitters and fixed sensors that are not moved once they are placed.

In this depicted example, transducer system 410 is a set of one or more transducers that is placed onto or within fuselage 402. Transducer system 410 may be attached to surfaces within fuselage 402 or may be embedded into the materials itself, depending on the particular implementation.

The different transducers within transducer system 410 are arranged to be capable of monitoring one or more areas within fuselage 402. These areas may be selected based on different factors, such as identifying areas in which damage may cause a failure within fuselage 402. In a similar fashion, transducer system 412 is attached to or integrated with components in engines 404. Transducer system 414 also is integrated and configured to collect data from one or more areas in wings 406.

Transducers within transducer systems 410, 412, and 414 are distributed on or within structure 400. This type of distribution is in contrast to the distribution that sensors use for tomographic imaging, in which the sensors are placed along the boundary of the structure. In these examples, the different sensors within transducer systems 410, 412, and 414 may be distributed over a grid on structure 400. This grid may be, for example, a square or hexagonal grid in which a sensor is located within each block or hexagon within the grid.

Transducer systems 410, 412, and 414 are controlled by data processing system 408. Data processing system 408 may send signals for transmission by these transducer systems. Further, the responses received in response these signals are returned to data processing system 408 for processing. The responses collected from transducer systems 410, 412, and 414 are compared to baseline or comparison signals.

The illustration of structure 400 in FIG. 4 is presented for the purposes of explaining one advantageous embodiment. This illustration is not meant to limit the manner in which different advantageous embodiments may be implemented or embodied. For example, in other advantageous embodiments, other numbers of transducer systems may be present. For example, structure 400 may include five, ten, twenty, or some other suitable number of transducer systems depending on the particular implementation. Also, additional data processing systems, in addition to data processing system 408, also may be present for redundancy.

Figure 5:
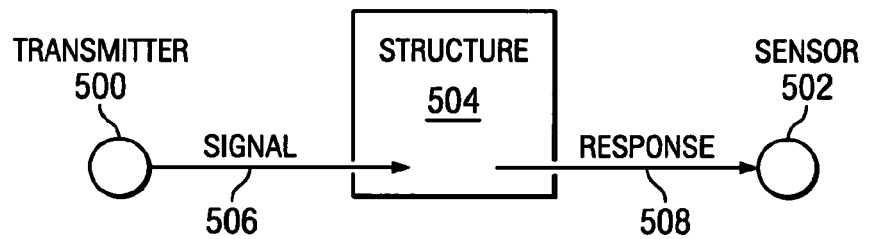
FIG. 5 is a diagram illustrating signal transmission and detection in accordance with an advantageous embodiment.

Turning now to FIG. 5, a diagram illustrating signal transmission and detection is depicted in accordance with an advantageous embodiment. In this example, transmitter 500 and sensor 502 may be used to test structure 504. Transmitter 500 and sensor 502 are examples of a transmitter and a sensor that may be found in transducer system 410 in FIG. 4. Structure 504 is an example of a structure that may be present in a structure, such as fuselage 402 or wings 406 in FIG. 4.

Transmitter 500 transmits or sends signal 506 into structure 504. Signal 506 is a waveform having a selected frequency range. Response 508 is detected by sensor 502. Response 508 is generated in response to the transmission of signal 506 into structure 504. Although, in this example, sensor 502 is shown as receiving response 508 on an opposite side of structure 504 from transmitter 500, sensor 502 may be located on the same side of structure 504 as transmitter 500. With this configuration, response 508 is detected from reflections or scattering of signal 506 being transmitted into structure 504.

Response 508 is used, in these different illustrative examples, in a comparison with a prior response to determine whether changes have occurred in structure 504. These changes may be anomalies that occur through various stresses and other environmental conditions to which structure 504 is subjected to over time.

Figure 6:
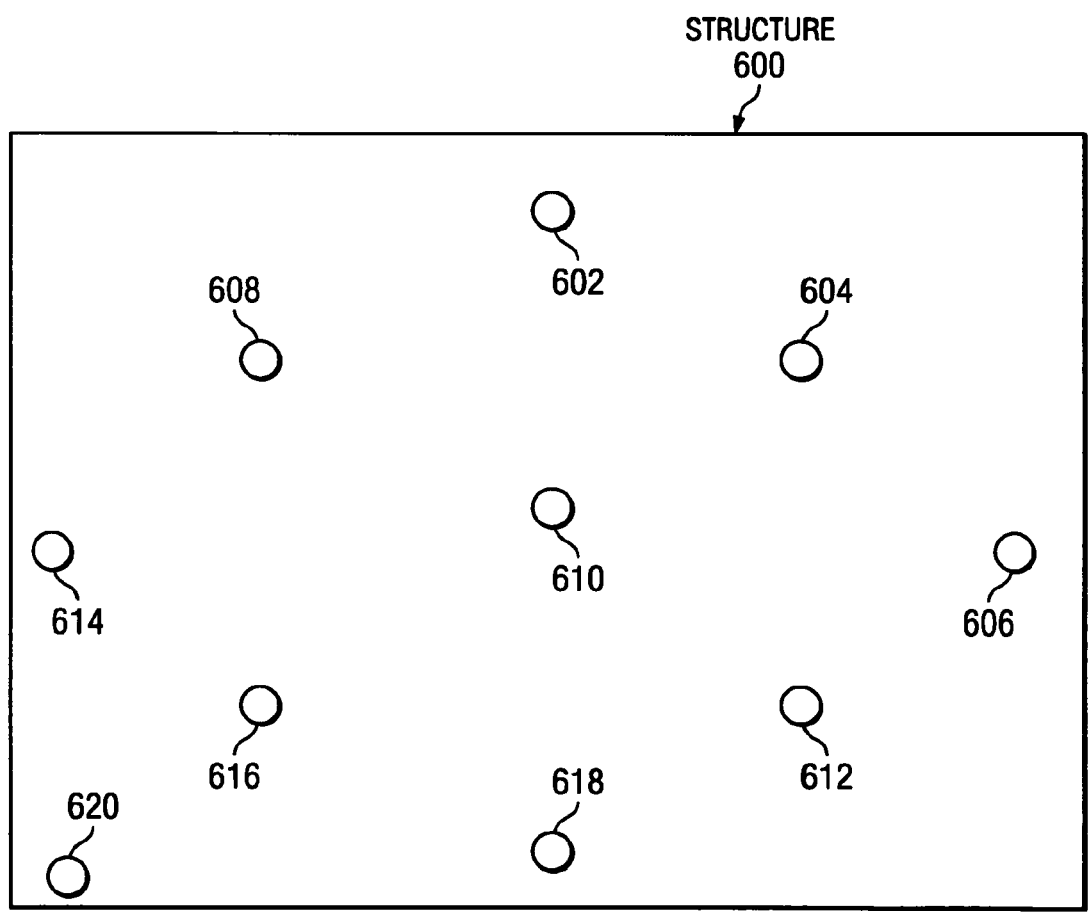
FIG. 6 is a diagram illustrating a distribution of sensors for a structure in accordance with an advantageous embodiment.

With reference now to FIG. 6, a diagram illustrating a distribution of sensors for a structure is depicted in accordance with an advantageous embodiment. In this example, structure 600 is an example of structure 400 or a portion of structure 400 in FIG. 4. In this example, sensors 602, 604, 606, 608, 610, 612, 614, 616, 618, and 620 are present within structure 600.

As can be seen, in this example, these sensors may be disbursed in an approximately uniform manner such that they may fall within a grid that formed having, for example, squares and/or hexagons. In these examples, the sensors may be separate from the transmitters or may be part of a transducer in performing both a transmitter and sensor functions. Sensors 602, 604, 606, 608, 610, 612, 614, 616, 618, and 620 may or may not be uniformly distributed within or on structure 600. Also, other number of sensors or arrangement of sensors may be used.

Figure 7:
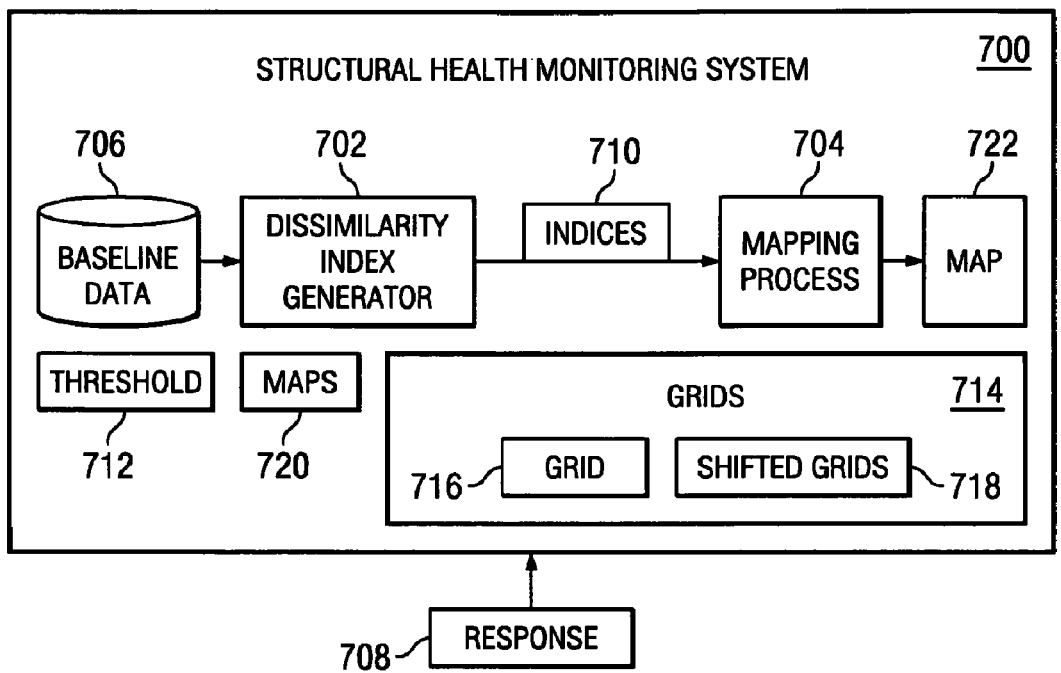
FIG. 7 is a diagram illustrating a health monitoring system in accordance with an advantageous embodiment.

With reference now to FIG. 7, a diagram of a structural health monitoring system is depicted in accordance with an advantageous embodiment. In this example, structural health monitoring system 700 includes dissimilarity index generator 702, mapping process 704, and baseline data 706. Dissimilarity index generator 702 may receive response 708 and compare response 708 to baseline data 706. This index is referred to as a dissimilarity index. This type of index is in contrast to a change metric. A change metric is a value associated or assigned to a particular portion of a map such as a pixel and/or portion of a grid.

Baseline data 706 may take the form of signals generated in response to interrogating the structure at a prior point in time. These signals also may be referred to as comparison signals. This prior point in time may be a time when the structure was first manufactured. Of course, baseline data 706 may contain signals for other points in time after the creation of the structure. These other points in time may be for when the structure is considered healthy. Dissimilarity index generator 702 may generate indices 710 and send this information to mapping process 704. Each index in indices 710 is an index identified for a particular path between a sensor and transmitter.

Mapping process 704 may identify an area of change for analysis within the structure based on determining whether any of indices 710 for particular paths are greater than threshold 712. Threshold 712 is a value over which a dissimilarity index within indices 710 is considered to be of interest or may indicate a change. In these examples, the path between a transmitter and a sensor having a dissimilarity index greater than a threshold is referred to as a path of interest.

Based on an identification of the paths of interest, mapping process 704 may generate grids 714. Grids 714 may encompass areas of the structure that contain the paths having dissimilarity indices with values above threshold 712. Additionally, this area of mapping may be constrained to specific areas. For example, the area may be constrained based on using only paths shorter than a specified length that are above threshold 712.

Grids 714 may contain one or more grids that are located within an area of interest. The area of interest may be identified based on the paths of interest. The area of interest may include the different paths of interest identified based on a comparison of indices 710 with threshold 712.

For example, grid 716 within grids 714 is a grid containing the area of interest based on a comparison of indices 710 to threshold 712. Mapping process 704 may identify a change metric for each pixel within grid 716 in grids 714 using a least-squares solution in these examples.

Mapping process 704 may select grid 716 to generate shifted grids 718 from grid 716, in which each grid in shifted grids 718 is shifted from grid 716. Change metrics are identified for the pixels within grid 716 and shifted grids 718. The identification of change metrics of the pixels in these grids may be used to form maps 720. These maps may not have a desired resolution.

Mapping process 704 may combine maps 720 to form map 722, which has a higher resolution than maps 720. In this manner, a better identification of changes within the structure may be made from map 722. In these examples, map 722 may be a two-dimensional or three-dimensional map.

Map 722 may be represented as an image depending upon a particular implementation. Map 722 identifies locations in which changes are present. Further, map 722 may include an indication of regions or volumes in which changes are present.

The illustration of the components for structural health monitoring system 700 in FIG. 7 are presented for purposes of depicting one manner in which structural health monitoring system 400 in FIG. 4 may be implemented. This example is not meant to limit the manner in which other advantageous embodiments may be implemented. For example, other advantageous embodiments may include other components in addition to or in place of the ones illustrated in FIG. 7.

Additionally, some components may be combined or further subdivided depending upon the particular implementation. For example, dissimilarity index generator 702 and mapping process 704 may be combined as a single component. In other advantageous embodiments, mapping process 704 may be subdivided into a grid generation process and a map generation process.

Figure 8:
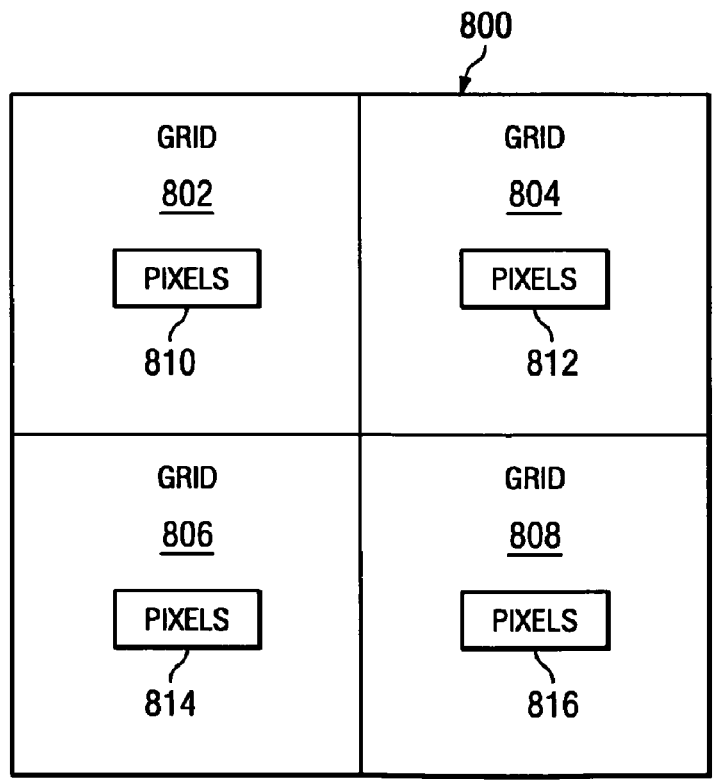
FIG. 8 is a diagram illustrating an area identified for mapping in accordance with an advantageous embodiment.

With reference now to FIG. 8, a diagram illustrating an area of a structure identified for mapping is depicted in accordance with an advantageous embodiment. In this example, area 800 is an example of an area within a structure containing paths with dissimilarity indices above a threshold level. These paths passing through area 800 may be processed to identify change metrics for particular pixels or portions of area 800.

In the different advantageous embodiments, area 800 is subdivided into grids 802, 804, 806, and 808. Grid 802 is subdivided into pixels 810, grid 804 is subdivided into pixels 812, grid 806 is subdivided into pixels 814, and grid 808 is subdivided into pixels 816. Pixels within grid 802 do not overlap each other. In a similar fashion, pixels within grid 806 do not overlap each other and pixels within grid 808 do not overlap each other. These pixels, however, may overlap other pixels in other grids.

In these examples, each of grids 802, 804, 806, and 808 may be processed in the manner described above with reference to FIG. 7. For example, grid 802 may be shifted such that a number of grids are generated with respect to grid 802. Each of these grids represents separate images for area 800 in these illustrative examples. Change metrics may be estimated for pixels in each of these grids. Each pixel within each of the grids may be assigned a value. This value may be estimated from the dissimilarity indices in the different paths that may pass through the different pixels.

Maps with a first resolution may be generated from these grids. A similar process may be performed with respect to grids 804, 806, and 808. These maps may be combined to form a map for grid 802 that has a higher resolution than the first resolution. An example of one manner in which these grids may be combined is to "up-sample" each map to increase sampling rates for individual maps. The up-sampled maps may then be combined to obtain a final resolution map. In this manner, a map of area 800 may be generated.

The description of area 800 and the subdivision into grids is provided for purposes of illustrating one manner in which the advantageous embodiments may be implemented. This illustration is not meant to limit the manner in which the different advantageous embodiments may be implemented. As one example, area 800 is illustrated as a rectangular area.

In other advantageous embodiments, area 800 may take other shapes such as, for example, a circle, a hexagon, a pentagon, a non-regular shape, or some other suitable shape. As another example, other numbers of grids may be created from area 800. For example, area 800 may have 2 grids, 8 grids, 20 grids, or some other suitable number of grids.

In another example, in other advantageous embodiments, a volume may be defined rather than area 800. With a volume, a three-dimensional map of the structure may be created.

Figure 9:
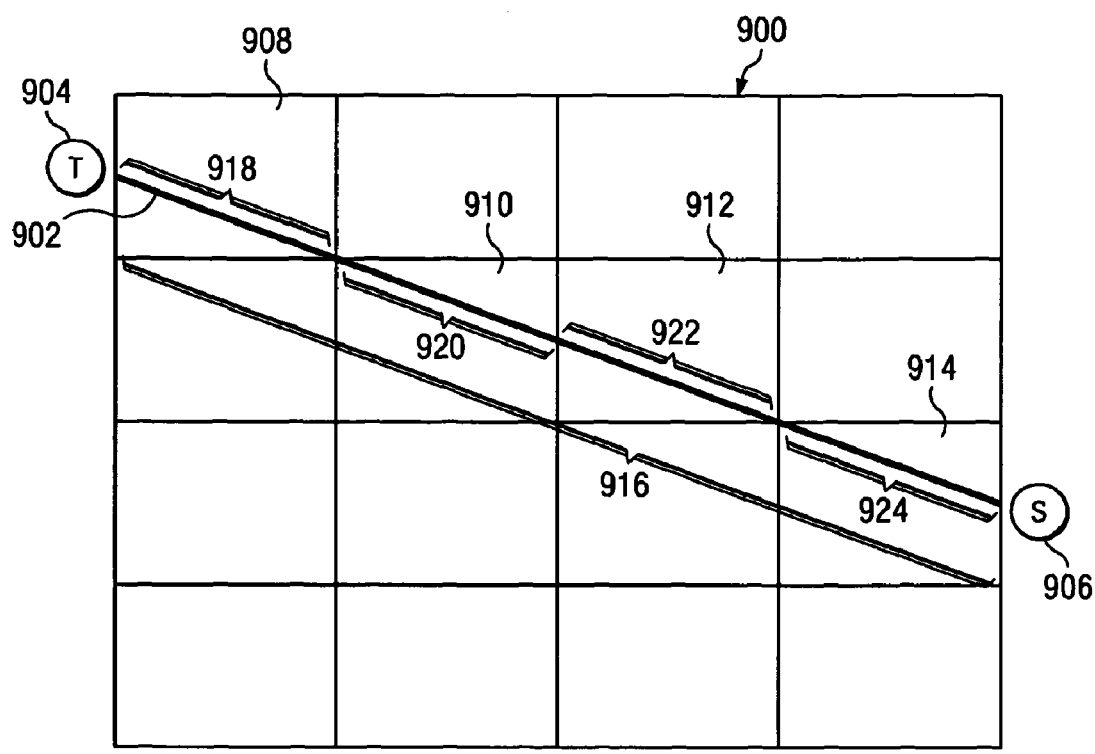
FIG. 9 is a diagram illustrating a path through a grid in accordance with an advantageous embodiment.

With reference now to FIG. 9, a diagram illustrating a path through a grid is depicted in accordance with an advantageous embodiment. In this example, grid 900 is shown with path 902 between transmitter 904 and sensor 906. As illustrated, path 902 passes through pixels 908, 910, 912, and 914. In these examples, a change metric may be generated for each of these pixels through which path 902 passes.

In this example, path 902 has length 916 and has a dissimilarity index. The dissimilarity index for path 902 may take the form of a single value. This value is a measure of a change in the structure of path 902 between transmitter 904 and sensor 906. A change metric may be estimated for pixels 908, 910, 912, and 914 based on the portion of length 916 passing through a particular pixel and the dissimilarity index for path 902.

Path 902 overlaps pixel 908 with length 918, pixel 910 with length 920, pixel 912 with length 922, and pixel 914 with length 924 in these illustrative examples. The change metric for each pixel is generated from the dissimilarity index of path 902 based on a proportion of the length of path 902 to length 916.

For example, assume path 902 has a change index of 10 and has a length of 10 cm. If length 918 is 2.5 cm, then pixel 908 may have a change metric of 2.5 if the change to the structure is identical in all pixels that the path passes through. In another example, if multiple paths pass through a pixel, then the change metric is identified from the contribution of each path passing through the pixel. With more complex situations in which multiple paths are present within a pixel, other techniques may be used to identify the contributions. These other techniques may include, for example, using a least-squares solution.

Figure 10:
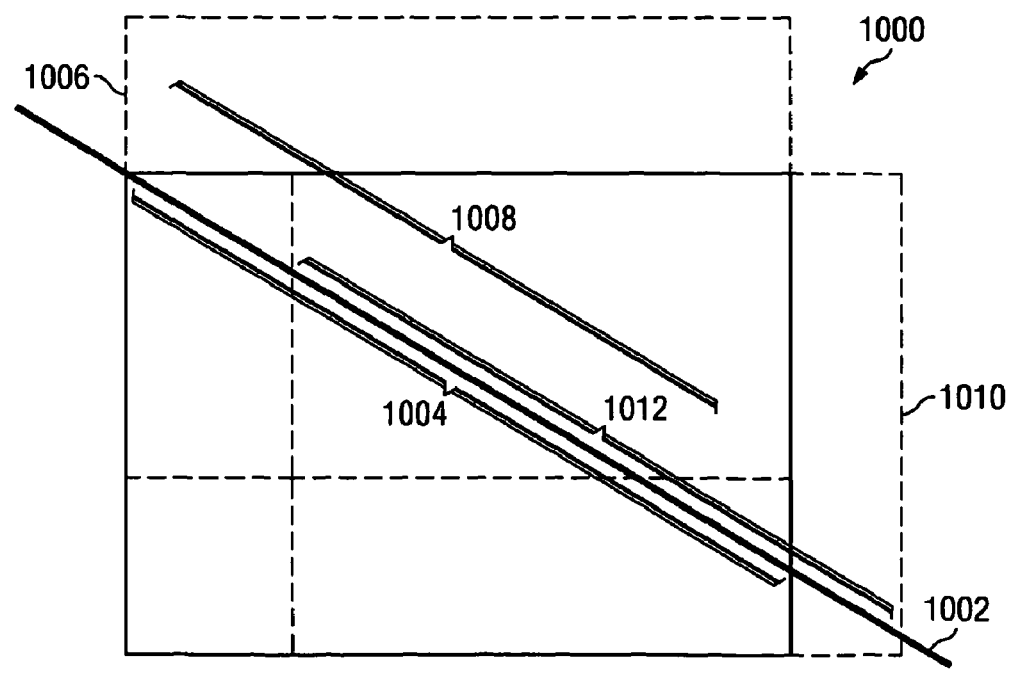
FIG. 10 is a diagram illustrating the shifting of a pixel in a grid in accordance with an advantageous embodiment.

With reference now to FIG. 10, a diagram illustrating the shifting of a pixel in a grid is depicted in accordance with an advantageous embodiment. In this example, pixel 1000 is an example of a pixel in a grid, such as grid 900 in FIG. 9.

Path 1002 passes through pixel 1000. Path 1002 has length 1004 within pixel 1000. When the grid containing pixel 1000 is shifted, pixel 1000 also shifts, although path 1002 does not shift. In other words, new pixels are defined when the grid shifts.

For example, shifted pixel 1006 is an example of a shifted pixel in a shifted grid. Path 1002 has length 1008 through shifted pixel 1006. In yet another example, pixel 1000 may be shifted to form shifted pixel 1010, which has length 1012 through shifted pixel 1010 for path 1002. As can be seen, lengths 1004, 1008, and 1012 may be different for path 1002 as pixel 1000 is shifted. The data is the same for path 1002 although the length of path 1002 may change when a grid is shifted.

As a result, the solution or identification of a change metric may change for a particular pixel when shifting occurs. This shifting may result in path 1002 passing though some pixels that path 1002 did not pass through before. The shifting also may result in path 1002 no longer passing through some pixels that path 1002 passed through before the shifting of the grid.

In this example, pixel 1000 is shown as being shifted in a horizontal and a vertical direction when a grid containing pixel 1000 is shifted. In other advantageous embodiments, the shifting may be in other directions. For example, pixel 1000 may rotate about an axis in addition to or in place of shifting pixel 1000 in a horizontal and/or vertical direction.

Figure 11:
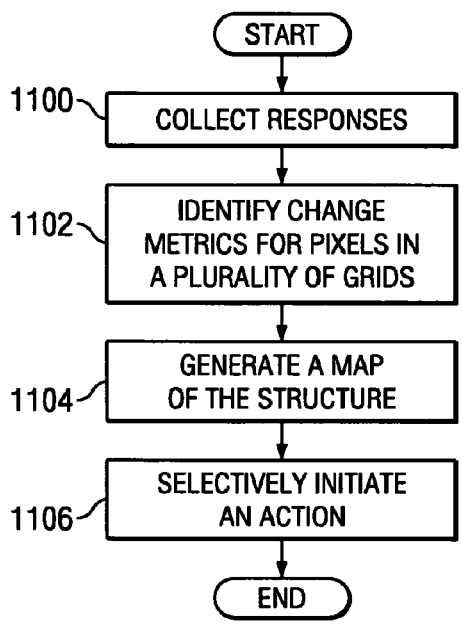
FIG. 11 is a flowchart of a process for mapping changes in a structure in accordance with an advantageous embodiment.

With reference now to FIG. 11, a flowchart of a process for mapping changes in a structure is depicted in accordance with an advantageous embodiment. The process illustrated in FIG. 11 may be implemented using a health monitoring system such as, for example, structural health monitoring system 700 in FIG. 7.

The process begins by collecting responses (operation 1100). These responses are signals received at a sensor in response to a signal being transmitted by a transmitter. The process identifies change metrics for pixels in a plurality of grids (operation 1102). In these examples, an index is identified for each pixel within a grid. The different grids may be shifted with respect to each other although the data remains the same with respect to the responses collected in operation 1100. In most cases, multiple paths pass through a pixel. Operation 1102 may involve identifying the contribution for each path passing through a pixel to identify a single change metric for that pixel.

By shifting the grids, the pixels also shift, which may result in a change in the length of a path in the shifted pixel. This difference in the length of the path may result in a different change metric being identified for a particular pixel.

The process generates a map of the structure using the change metrics identified for the pixels (operation 1104). In the different advantageous embodiments, this map is identified by generating maps for each of the grids and then combining those maps. The process then selectively initiates an action (operation 1106), with the process terminating thereafter. This action may be to display the map, store the map, send an alert, and/or perform some other action. The map generated in operation 1104 maybe a two-dimensional or three-dimensional map, depending upon the particular implementation.

Figure 12:
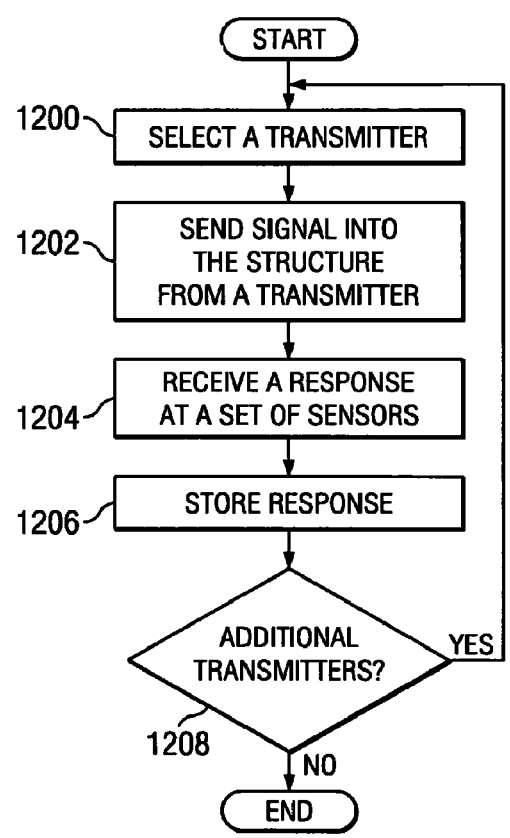
FIG. 12 is a flowchart of a process for obtaining responses in accordance with an advantageous embodiment.

With reference now to FIG. 12, a flowchart of a process for obtaining responses is depicted in accordance with an advantageous embodiment. The process illustrated in FIG. 12 is a more detailed example of operation 1100 in FIG. 11.

The process begins by selecting a transmitter (operation 1200). Thereafter, a signal is sent into the structure by the transmitter (operation 1202). The process receives a response at a set of sensors (operation 1204). The process then stores the response (operation 1206). Operation 1206 may store the response as a set of paths. Each path is an identification of the path between the transmitter and the sensor receiving the response. Each path may have a length as well as direction or orientation to identify the path within a structure. This path also may be characterized based on the location of the transmitter and the sensor.

The process determines whether additional transmitters should be used to transmit signals (operation 1208). If additional transmitters should be activated, the process returns to operation 1200. Otherwise, the process terminates. The result of the processes in FIG. 12 is the generation of paths for use in mapping changes.

Figure 13:
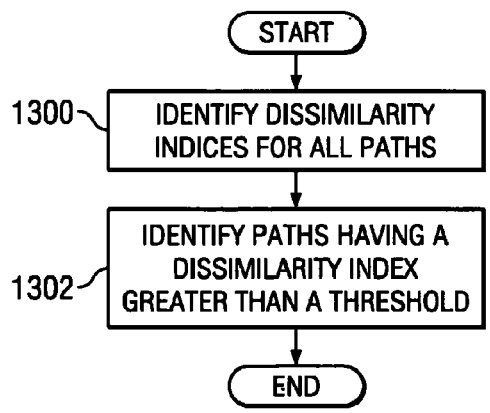
FIG. 13 is a flowchart of a process for identifying a general location of a change in a structure in accordance with an advantageous embodiment.

With reference now to FIG. 13, a flowchart of a process for identifying a general location of a change in a structure is depicted in accordance with an advantageous embodiment. When a change is present in a structure, the change may be in multiple locations. The process illustrated in FIG. 13 may be used to identify an area in which change may be analyzed in more detail. After the area is identified, advantageous embodiments may use all paths present for the analysis and not just ones with a dissimilarity index higher than a threshold. The process illustrated in FIG. 13 may be implemented as a part of the process for identifying change metrics for pixels in grids in operation 1102 in FIG. 11.

The process begins by identifying changes indices for all of the paths (operation 1300). Operation 1300 assigns a dissimilarity index to each path that has been stored in these examples. The process then identifies all paths that have a dissimilarity index greater than a threshold (operation 1302), with the process terminating thereafter.

Figure 14:
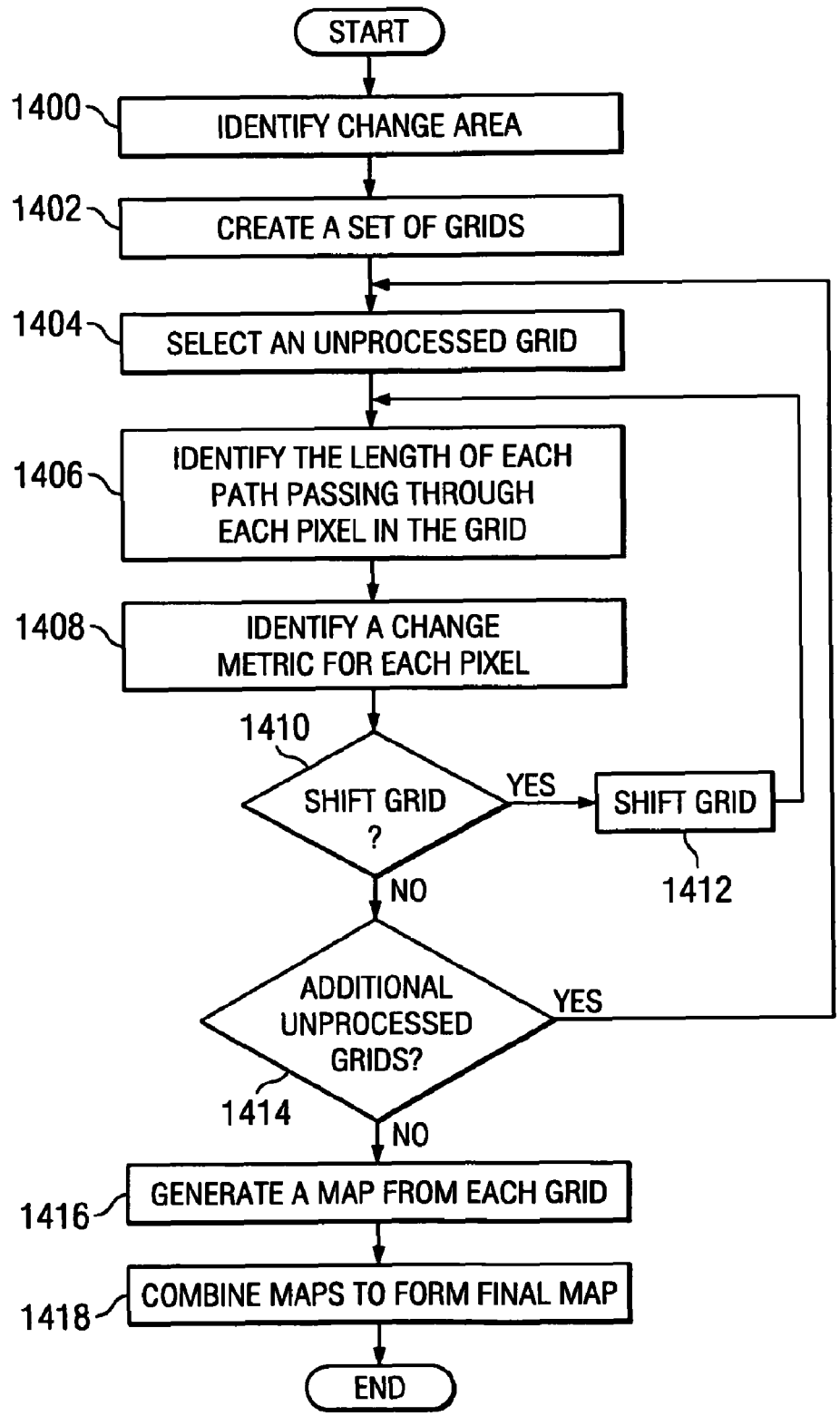
FIG. 14 is a flowchart of a process for creating a map from identified paths in accordance with an advantageous embodiment.

With reference now to FIG. 14, a flowchart of a process for creating a map from paths is depicted in accordance with an advantageous embodiment. The process illustrated in FIG. 14 may be implemented in a health monitoring system such as, for example, structural health monitoring system 700 in FIG. 7. In particular, the flowchart in FIG. 14 is a more detailed description of operation 1104 in FIG. 11. The process in FIG. 14 assumes that any non-working and/or damaged transducers are not taken into account in generating a map.

The process begins by identifying a change area (operation 1400). This change area may be a coarse localization in which all of the paths having a dissimilarity index above a threshold may be considered as part of the area. In other advantageous embodiments, the change area may be constrained based on selecting paths shorter than a specified length that have dissimilarity index values above the threshold area.

The process creates a set of grids from the change area (operation 1402). This set of grids may be a set of rectangular grids that fit within the change area. Of course, the grids may take other forms other than rectangles. In some examples, the grid may be triangular, hexagonal, circular, or even irregular shaped.

Further, different shapes of grids may be used to cover the change area. Each grid within the set of grids contains a number of grid elements referred to as pixels.

The process selects an unprocessed grid from the set of grids for processing (operation 1404). The process then identifies the length of each path passing through each pixel in the selected grid (operation 1406). The distance or length of the path between a transmitter and a sensor may be measured. Based on knowing this length, the portion of the path passing through a particular pixel in a grid may be identified.

A change metric is identified for each pixel in the grid (operation 1408). In other words, operation 1408 identifies a change metric for each pixel through which the path passes. In these examples, each pixel in a grid may have a default value if a path does not pass through the grid. For example, a change metric value of 0 may be assigned to all of the pixels in all of the grids in which the dissimilarity index value of 0 indicates that no change is present.

Then, these values may be altered based on paths passing through some of the pixels. Of course, the selection of values in these examples is presented for purposes of illustrating one manner in which a change metric may be implemented. Other change metrics may use other values to indicate whether a change has occurred and the amount of change.

If changes are present in the path, particular pixels within the path also may have a different change metric indicating that a change is present. For example, a pixel may have a change metric of 1 to indicate that a change is present in that pixel as opposed to an index of 0.

In identifying a change index for each pixel, a least-squares solution may be used to estimating these values. In these examples, all portions or points in a pixel are represented by a single value for the change metric. In other words, any change is assumed to be the same throughout all points within a pixel. With this type of assumption, the estimated change metric for each pixel represents an average characterization of the change associated with all locations within the pixel.

Assume l(i,j,m) represents the length of the (i,j)th path that passes through the mth pixel in the grid, and d(m) is the change metric associated with the mth pixel. Assuming a linear relationship between the change metric of pixels and the dissimilarity index of paths and assuming that the contribution of each pixel to the dissimilarity index is proportional to the length of the path passing through the pixel along with the change metric of the pixel, the dissimilarity index D(i,j) for the (i,j)th path may be related to d(m) and l(i,j,m) using the following relationship:

$$D(i, j) = \sum_{m=1}^{M} d(m)l(i, j, m)$$

When the number of transducers on the structure is sufficiently large, more equations than unknowns (d(m)) are present in the above set of equations. In these situations, the change metrics may be solved by using a least-squares method or some other technique.

The process then determines whether the grid should be shifted (operation 1410). If the grid should be shifted, the process shifts the grid (operation 1412). In these examples, the amount of shift may be any amount that is smaller than a pixel size. The shifting may be in various directions. This shifting may be, for example, horizontal or vertically with respect to a view of the grid. In other advantageous embodiments, the grid may be rotated instead of or in addition to shifting the grid vertically or horizontally. The process then returns to operation 1406 as described above.

With reference again to operation 1410, if the grid is not to be shifted, the process determines whether additional unprocessed grids are present (operation 1414). If additional unprocessed grids are present, the process returns to operation 1404.

Otherwise, the process generates a map from each grid (operation 1416). This map may be, for example, a map identifying change metrics for each pixel. These change metrics may be presented as, for examples, numbers, colors, graphic indicators, and/or other suitable presentation mechanism. In these examples, the different change metrics form the maps.

The process combines the maps to form a final map (operation 1418) with the process terminating thereafter. Operation 1418 may combine the different maps for a grid and the shifted grids from that map to form a higher resolution map. One manner in which the maps may be combined is to interpolate each map over a higher density sampling grid and then average all of the interpolated maps.

The geometric means of the interpolated maps may also be used for this purpose. Of course, any other available or known technique for combining lower resolution maps into higher resolution maps may be used. Additionally, operation 1418 may combine all of these different maps to form a map for the overall change area. The combination of these different maps is referred to as a change metrics map.

Figure 15:
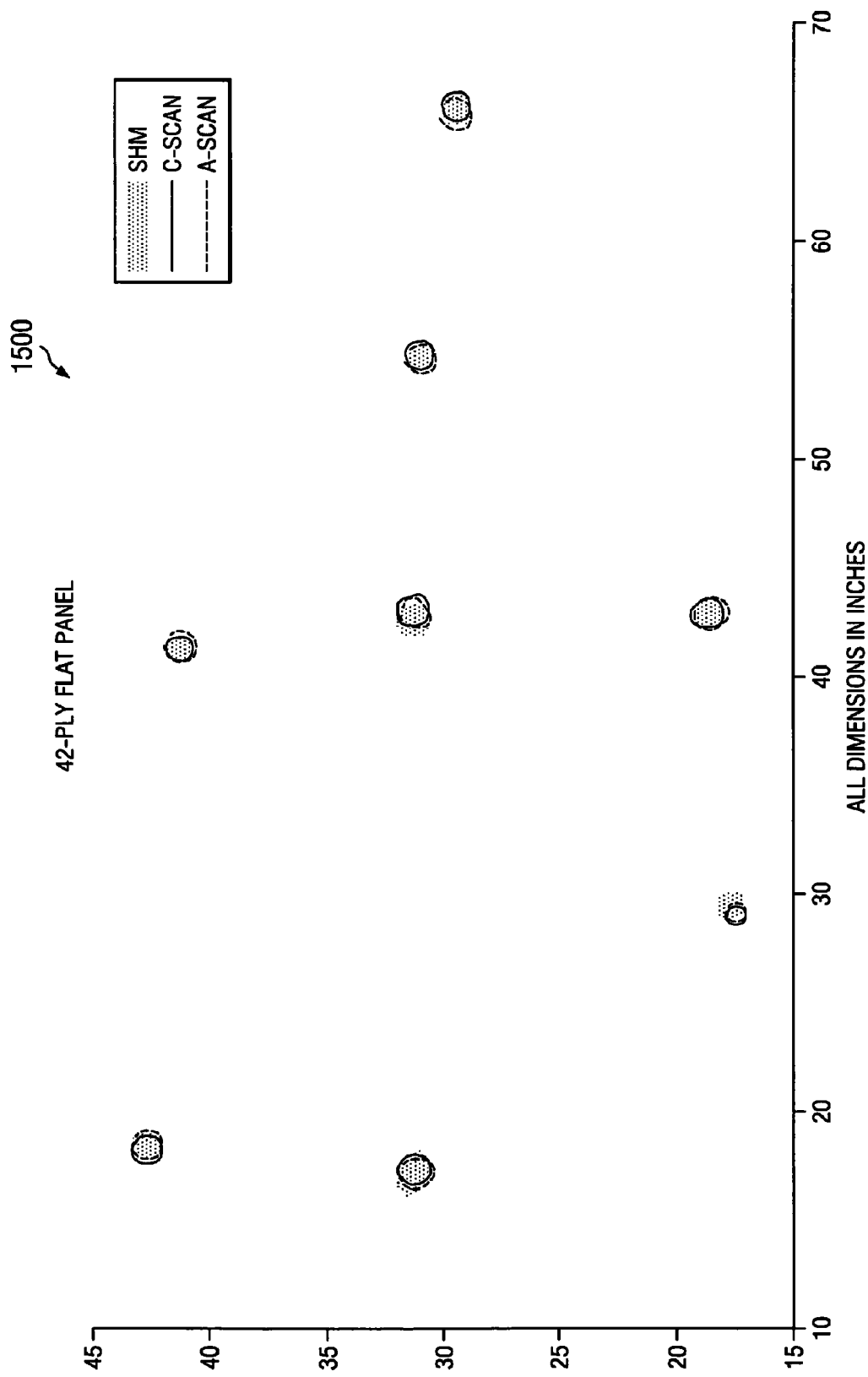
FIG. 15 is a graph illustrating example results from testing a structure in accordance with an advantageous embodiment.

With reference now to FIG. 15, a graph illustrating example results from testing a structure is depicted in accordance with an advantageous embodiment. In this example, graph 1500 is generated based on a test performed on a structure in the form of a composite panel. In this example, the composite panel is a 42-ply composite panel.

Graph 1500 shows the dimensions in inches. The x-axis shows a length of a panel, while the y-axis shows a width of the panel in these examples. In these examples, results are shown from ultrasound non-destructive evaluation (NDE) techniques involving c-scan and a-scan systems, and from using an advantageous embodiment. Traditional techniques are able to provide accurate results in general, but require extensive expert human involvement. Therefore, these types of techniques are slow and expensive.

Figure 16:
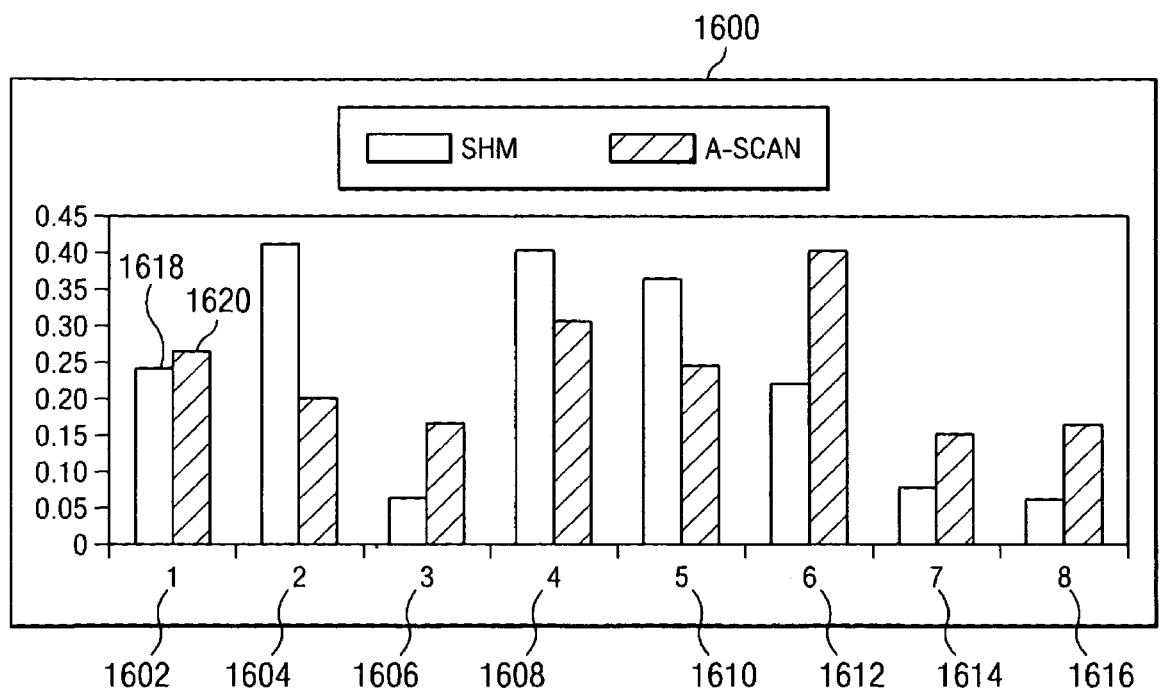
FIG. 16 is a graph illustrating changes in a structure in accordance with an advantageous embodiment.

With reference now to FIG. 16, a graph illustrating changes in a structure is depicted in accordance with an advantageous embodiment. Graph 1600 is a display of results from graph 1500 in FIG. 15 in a different form. In this example, graph 1600 takes the form of a bar graph. The bars in graph 1600 correspond to the eight different changes caused by the impacts shown in FIG. 15.

In these examples, the plain bars illustrate the results using an advantageous embodiment, while the cross-hatch bars illustrate a result from an a-scan. For example, bar 1618 shows a result from an advantageous embodiment while bar 1620 shows a result from an a-scan. The y-axis in graph 1600 represents the maximum difference in inches of the change outlines estimated by each technique from those estimated by a c-scan.

As can be seen from graph 1600, in 5 out of 8 cases, a monitoring system employing the advantageous embodiment provides a better identification of changes than a system using an a-scan. In these examples, impacts 1602, 1604, 1606, 1608, 1610, 1612, 1614, and 1616 are shown. Impacts 1602, 1606, 1612, 1614, and 1616 show a better identification as compared to using an a-scan. As a result, the quality of estimating changes is comparable to that of a traditional a-scan system without the extensive time and human involvement needed with a-scan systems.

Figure 17:
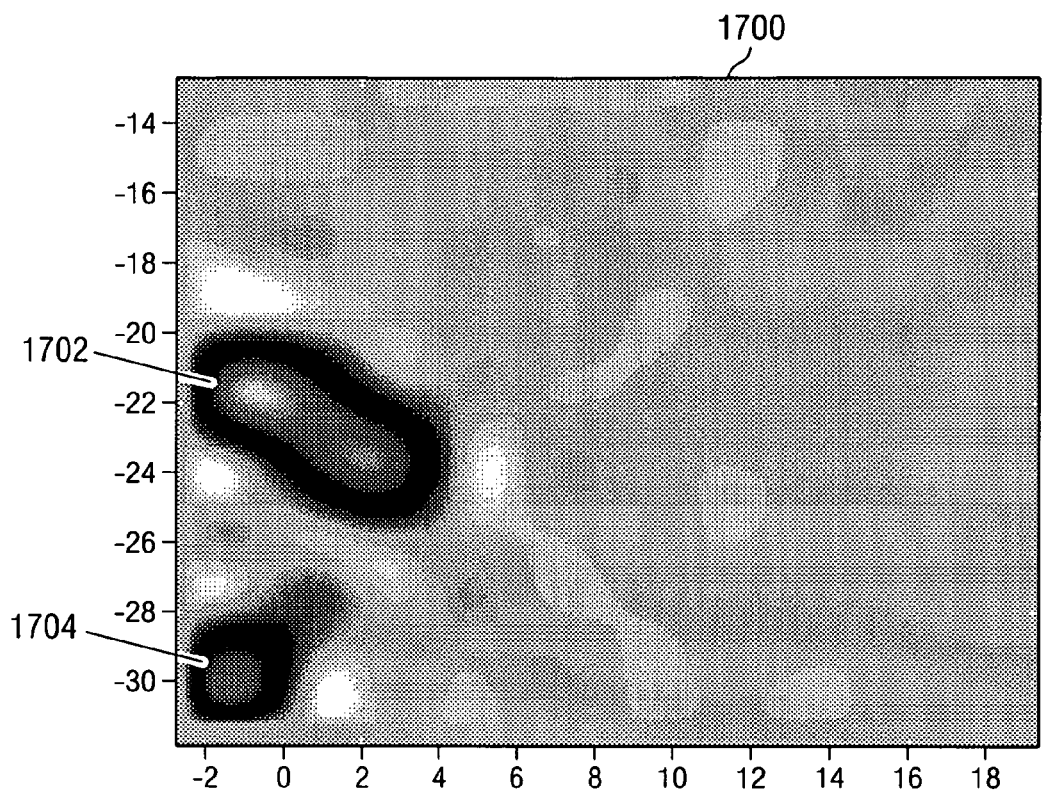
FIG. 17 is an image created from a grid in accordance with an advantage embodiment.

With reference now to FIG. 17, an example of an image created from a grid is depicted in accordance with an advantage embodiment. In this example, the location of the impact and the center of the change caused by the impact are approximately at the coordinates (1.5,−23) at section 1702 in the coordinate system used in the figure. The units are in inches. The shape of the change was approximately circular.

In this example, image 1700 is an example of an image created from 1 out of 25 grids for a structure. Image 1700 is a single grid. While image 1700 is able to show significant change at the location of the actual damage, image 1700 also shows a possible change erroneously at the bottom left-hand corner of the image. Furthermore, the shape of the change displayed at the location of the actual damage is oblong rather than circular. Combining several images obtained from different grids mitigates such erroneous characterizations of change in the structure.

Figure 18:
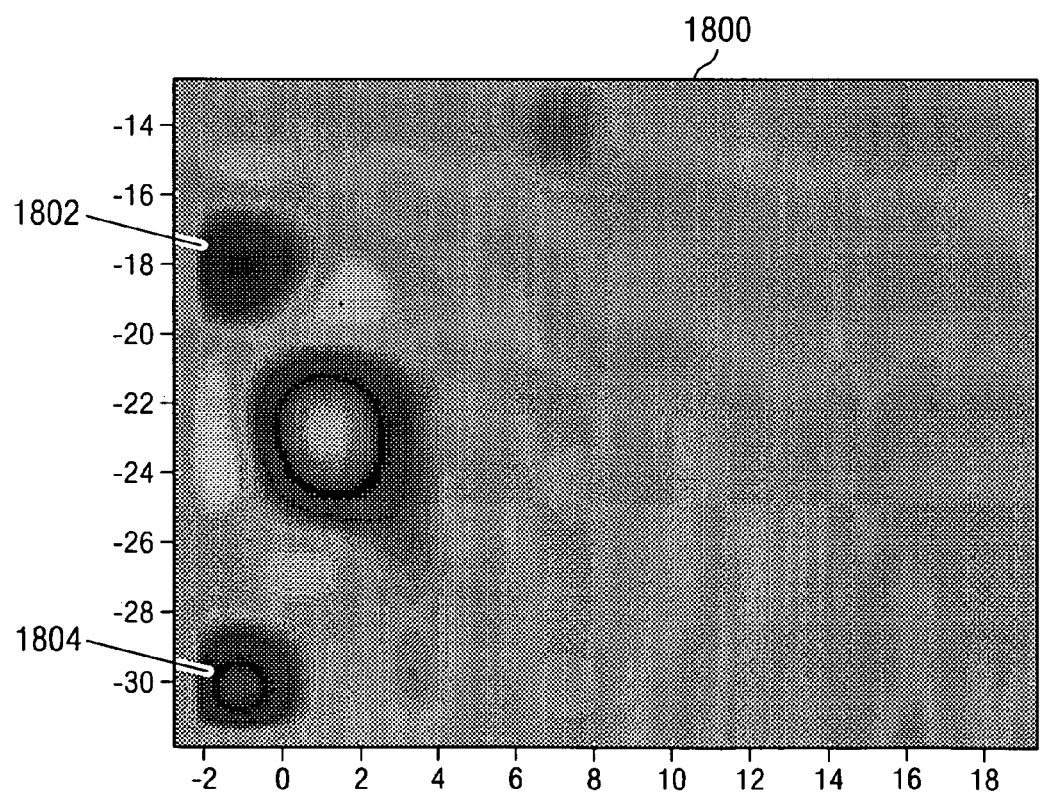
FIG. 18 is an image created from a grid in accordance with an advantageous embodiment.

With reference now to FIG. 18, an image created from a grid is depicted in accordance with an advantageous embodiment. In this example, image 1800 is an example of a 7th grid out of 25 grids in accordance with an advantageous embodiment. In this figure, changes are erroneously indicated in two locations in sections 1806 and 1804 outside the location of impact.

Figure 19:
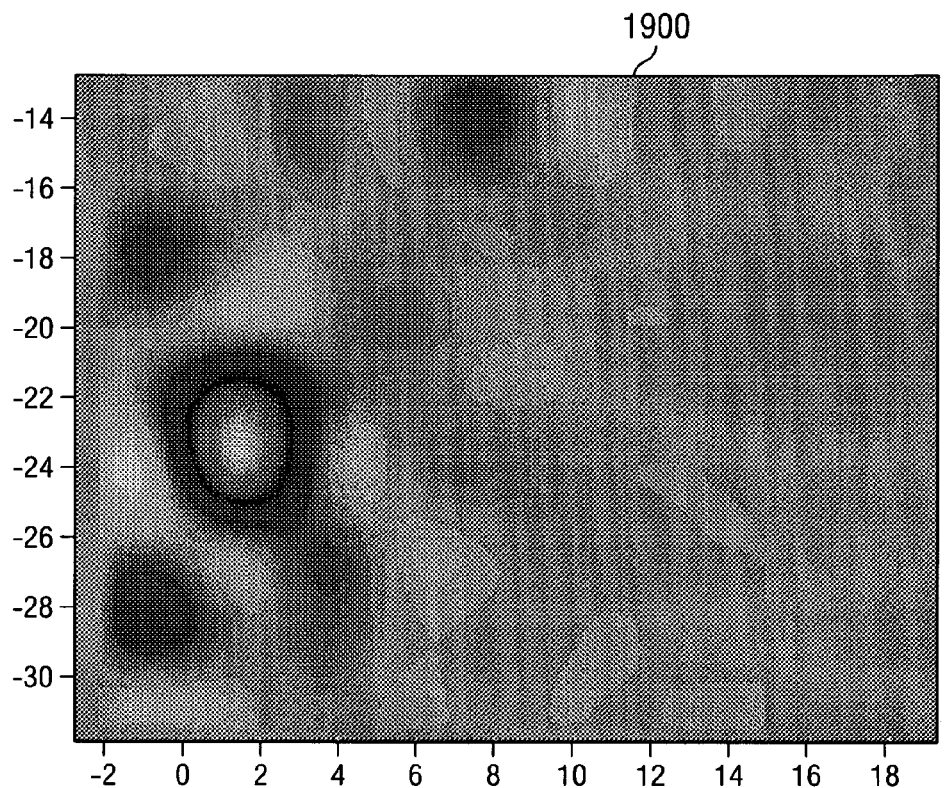
FIG. 19 is an image created from a grid in accordance with an advantageous embodiment.

With reference now to FIG. 19, a diagram illustrating an image created from a grid is depicted in accordance with an advantageous embodiment. In this example, image 1900 is an example of a 12th grid out of 25 grids created in accordance with an advantageous embodiment.

Figure 20:
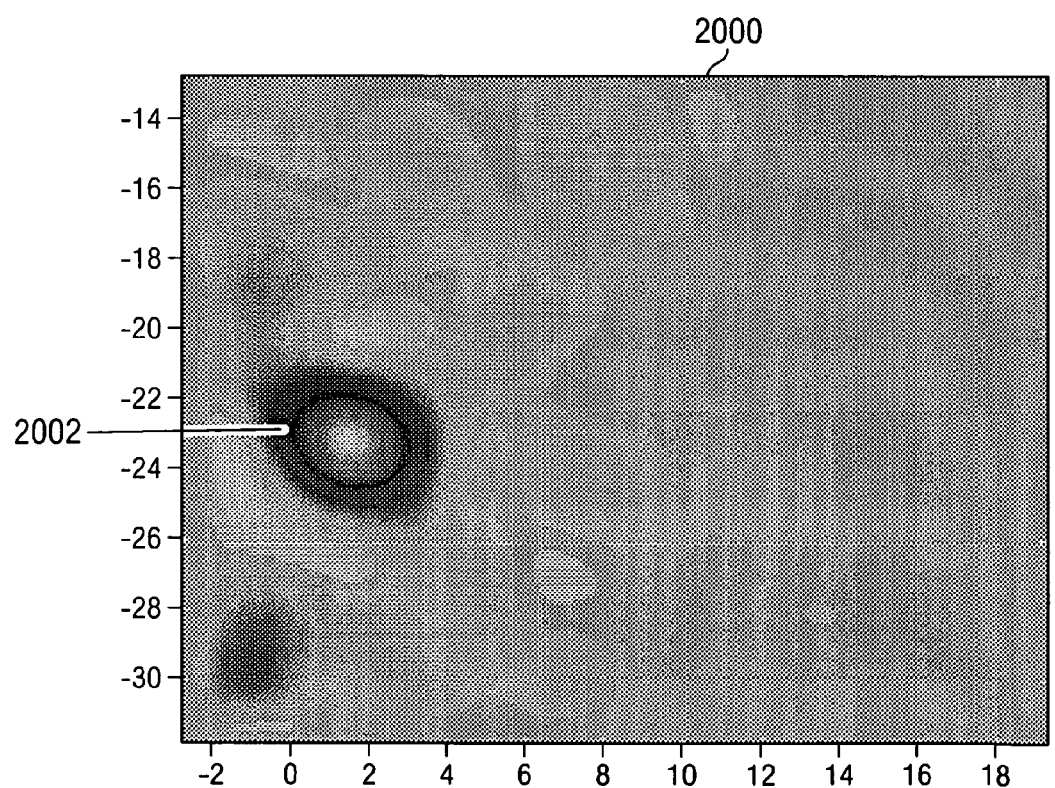
FIG. 20 is an example of an image generated from combining other images in accordance with an advantageous embodiment.

With reference now to FIG. 20, an example of an image generated from combining other images is depicted in accordance with an advantageous embodiment. In this example, image 2000 is an example of an image created from images, such as image 1700 in FIG. 17, image 1800 in FIG. 18, and image 1900 in FIG. 19. In this example, image 2000 is created from 25 images. The change indicated by this map is in the correct location as shown in section 2002 and has the right shape. This result indicates that combining change maps from multiple grids reduces and even eliminates many problems found in the results obtained using a single grid.

Thus, the different advantageous embodiments provide a method and apparatus for mapping changes in a structure. In these examples, responses are collected from a set of transmitter and sensor pairs for the structure. Change metrics are identified for pixels in a plurality of grids from the responses. A first grid in the plurality of grids is shifted in relation to a second grid in the plurality of grids. A map may be generated for the structure using the change metrics. In these examples, the change metrics for each grid may form an image with a first resolution. A final image with a greater resolution may be generated by combining the grids with the first resolution.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

Furthermore, the different embodiments can take the form of a computer program product accessible from a computer-usable or computer-readable medium providing program code for use by or in connection with a computer or any device or system that executes instructions. For the purposes of this disclosure, a computer-usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non limiting examples of a computer-readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W) and DVD.

Further, a computer-usable or computer-readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation to keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters are just a few of the currently available types of communications adapters.

The description of the different advantageous embodiments has been presented for purposes of illustration and description, and is not intended to be exhaustive or limited to the embodiments in the form disclosed. Many modifications and variations will be apparent to those of ordinary skill in the art.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for mapping changes in a structure, the method comprising:

collecting a plurality of responses from a set of transmitter and sensor pairs for the structure, the plurality of responses comprising responses to signals in a waveform with a frequency range selected to map the changes in the structure;

identifying on a computer change metrics for pixels in a plurality of grids from the plurality of responses, wherein a first grid in the plurality of grids is shifted in relation to a second grid in the plurality of grids, the identifying comprising:

finding a length of a path passing through a pixel in an unprocessed grid;

obtaining a solution for a change metric in a set of pixels to estimate a set of change metrics for the unprocessed grid; and repeating the finding and obtaining steps until the plurality of grids have been processed to obtain a plurality of sets of change metrics that are combined to form a final change metrics map for the structure; and generating on the computer a map for the structure using the change metrics.

2. The method of claim 1, wherein the collecting step comprises:

transmitting a signal from a transmitter in the set of transmitter and sensor pairs; and detecting the plurality of responses at a set of sensors in the set of transmitter and sensor pairs.

3. The method of claim 1, wherein the identifying step further comprises selecting an unprocessed grid in the plurality of grids;

wherein the step of finding a length comprises finding a length of each path passing through each pixel in the unprocessed grid;

and wherein the step of obtaining a solution comprises obtaining a least-squares solution for a change metric in each pixel to estimate a set of change metrics for the unprocessed grid; and repeating the selecting, finding, and obtaining steps until all of the plurality of grids have been processed to obtain a plurality of sets of change metrics that are combined to form a final change metrics map for the structure.

4. The method of claim 1, wherein the map identifies locations in which changes in the structure are present.

5. The method of claim 1, wherein the map identifies an identification of areas in the structure in which changes are present.

6. The method of claim 1, wherein the structure is selected from one of an aircraft, a building, a dam, a submarine, a spacecraft, a ship, a truck, a tank, a bridge, and a wall.

7. An apparatus comprising:

a structure having a set of components;

a set of transmitters physically associated with the set of components, wherein the set of transmitters is capable of sending signals into the set of components;

a set of sensors physically associated with the set of components, wherein the set of sensors is capable of detecting a response to the signals; and a data processing system in communication with the set of transmitters and the set of sensors, wherein the data processing system is capable of collecting a plurality of responses from the set of transmitters and the set of sensors, the plurality of responses comprising responses to the signals in a waveform with a frequency range selected to map the structure; identifying change metrics for pixels in a plurality of grids from the plurality of responses, wherein a first grid in the plurality of grids is shifted in relation to a second grid in the plurality of grids, the identifying comprising:

finding a length of a path passing through a pixel in an unprocessed grid;

obtaining a solution for a change metric in a set of pixels to estimate a set of change metrics for the unprocessed grid; and repeating the finding and obtaining steps until the plurality of grids have been processed to obtain a plurality of sets of change metrics that are combined to form a final change metrics map for the structure; and generating a map for the structure using the change metrics.

8. The apparatus of claim 7, wherein in collecting the plurality of responses from the set of transmitters for the structure, the data processing system is capable of transmitting a signal from a transmitter in the set of transmitters and detecting the plurality of responses at the set of sensors.

9. The apparatus of claim 7, wherein in identifying the change metrics for the pixels in the plurality of grids from the plurality of responses, the data processing system is capable of selecting an unprocessed grid in the plurality of grids; finding a length of each path passing through each pixel in the unprocessed grid; obtaining a least squares solution for a change in each pixel to form a set of change metrics for the unprocessed grid; and repeating the selecting, finding, and obtaining until all of the plurality of grids have been processed to obtain a plurality of sets of change metrics to form the change metrics.

10. The apparatus of claim 7, wherein the map identifies locations in the structure in which changes are present.

11. The apparatus of claim 7, wherein the map identifies an identification of areas in the structure in which changes are present.

12. The apparatus of claim 7, wherein the set of transmitters and the set of sensors are a set of transducers.

13. The apparatus of claim 7, wherein a transmitter and a sensor in the set of transmitters and the set of sensors are comprised of a single device that transmits a signal in a first mode and then changes to a second mode to detect a response to the signal.

14. The apparatus of claim 7, wherein the structure is selected from one of an aircraft, a building, a dam, a submarine, a spacecraft, a ship, a truck, a tank, a bridge, and a wall.

15. A computer program product comprising:

a nontransitory computer readable storage medium;

program code, stored on the storage medium, for collecting a plurality of responses from a set of transmitter and sensor pairs for a structure, the plurality of responses comprising responses to signals in a waveform with a frequency range selected to map the structure;

program code, stored on the storage medium, for identifying change metrics for pixels in a plurality of grids from the plurality of responses, wherein a first grid in the plurality of grids is shifted in relation to a second grid in the plurality of grids, the identifying comprising:

finding a length of a path passing through a pixel in an unprocessed grid;

obtaining a solution for a change metric in a set of pixels to estimate a set of change metrics for the unprocessed grid; and repeating the finding and obtaining steps until the plurality of grids have been processed to obtain a plurality of sets of change metrics that are combined to form a final change metrics map for the structure; and program code, stored on the storage medium, for generating a map for the structure using the change metrics.

16. The computer program product claim 15, wherein the program code for identifying the change metrics for the pixels in the plurality of grids from the plurality of responses comprises:

program code, stored on the storage medium, for selecting an unprocessed grid in the plurality of grids;

program code, stored on the storage medium, for finding a length of each path passing through each pixel in the unprocessed grid;

program code, stored on the storage medium, for obtaining a least squares solution for a change in each pixel to form a set of change metrics for the unprocessed grid; and repeating the program code for selecting the unprocessed grid in the plurality of grids;

finding the length of the each path passing through the each pixel in the unprocessed grid;

obtaining the least squares solution for the change in the each pixel to form the set of change metrics for the unprocessed grid until all of the plurality of grids have been processed to obtain a plurality of sets of change metrics to form the change metrics.

\* \* \* \* \*